(12) United States Patent
Carichon et al.

(10) Patent No.: US 8,171,807 B2
(45) Date of Patent: May 8, 2012

(54) ISO-KINETIC PROBE FOR THE ANALYSIS OF THE POLLUTION OF GASES GENERATED BY AN AIRCRAFT ENGINE

(75) Inventors: Sebastien Carichon, Saint Thibaut (FR); Serge Del Arco, Hericy (FR); Nadine Alice Helene Harivel, Vaux le Penil (FR)

(73) Assignee: SNECMA, Paris (FR)

( * ) Notice: Subject to any disclaimer, the term of this patent is extended or adjusted under 35 U.S.C. 154(b) by 798 days.

(21) Appl. No.: 12/256,130

(22) Filed: Oct. 22, 2008

(65) Prior Publication Data
US 2010/0043573 A1 Feb. 25, 2010

(30) Foreign Application Priority Data
Oct. 31, 2007 (FR) ...................................... 07 58751

(51) Int. Cl.
*G01N 1/22* (2006.01)
(52) U.S. Cl. ................ 73/863.51; 73/863.58; 73/863.85
(58) Field of Classification Search ............... 73/863.51, 73/863.58, 863.85
See application file for complete search history.

(56) References Cited

U.S. PATENT DOCUMENTS

| | | | |
|---|---|---|---|
| 3,252,323 A | 5/1966 | Torgeson | |
| 3,395,516 A | 8/1968 | Schecter et al. | |
| 3,965,748 A * | 6/1976 | Boubel et al. | 73/863.03 |
| 4,034,611 A | 7/1977 | Horling | |
| 4,276,092 A * | 6/1981 | St. John et al. | 106/751 |
| 6,555,385 B1 * | 4/2003 | Honda et al. | 73/31.03 |
| 6,807,844 B2 * | 10/2004 | Kogure et al. | 73/28.01 |
| 7,610,793 B2 * | 11/2009 | Liu et al. | 73/863.51 |

FOREIGN PATENT DOCUMENTS
FR 2141220 1/1973
* cited by examiner

*Primary Examiner* — Hezron E Williams
*Assistant Examiner* — Nashmiya Fayyaz
(74) *Attorney, Agent, or Firm* — Oblon, Spivak, McClelland, Maier & Neustadt, L.L.P.

(57) ABSTRACT

An iso-kinetic probe for the analysis of the pollution of the gases generated by an aircraft engine is disclosed. The probe includes an air tapping tube having an upstream end inserted into a conduit wherein a gas stream flows and a gas stream inlet velocity adjustment device provided at an orifice of the tapping tube. The tube has a downstream end mounted in a fixed manner on a base. The base has an outer diameter mounted in an inner diameter d of a passage bushing. The inner diameter d of the passage bushing being sufficiently great so that the upstream end of the tube is suitable to fit through the inner diameter of the passage bushing. The probe also includes a measurement chamber having an end connected to the base.

9 Claims, 5 Drawing Sheets

ISO-KINETIC PROBE FOR THE ANALYSIS OF THE POLLUTION OF GASES GENERATED BY AN AIRCRAFT ENGINE

FIELD OF THE INVENTION

The invention relates to an iso-kinetic probe, particularly for the analysis of the pollution of gases generated by an aircraft engine, comprising an air tapping tube having an upstream end inserted into a conduit wherein a gas stream flows, gas stream inlet velocity adjustment means being provided at an orifice of the tapping tube.

In airliners, the cabin pressurisation air is supplied by tapping performed on the compressed air by the engines. For this reason, it is necessary to verify that this air is free from pollutants which would render it unfit for breathing by the cabin passengers.

Measurement probes for the analysis of the pollution of the gases generated by an aircraft engine are known. These probes are iso-kinetic. This means that the air flows at the same velocity in the tapping end of the probe and in the air stream wherein tapping is performed. Fittings of three different diameters are provided, it being understood that the inlet velocity of the air in the fitting increases when the diameter of the tapping hole decreases at intake iso-flow. Alternatively or in addition, the tapping tube inlet adjustment is obtained by means of a pumping system downstream from the probe.

With such a probe, the intake velocity is known with a significant lack of precision. In addition, changing the fitting requires the disassembly of the sampling tube. However, this disassembly is inconvenient and time-consuming. In addition, it is necessary to test the tightness of the connection of the probe on the test pipes after reassembly.

The aim of the present invention is to remedy these drawbacks by proposing an iso-kinetic probe that is easy to disassemble and reassemble and wherein the air intake velocity may be known with a satisfactory precision.

These aims are achieved according to the invention in that the tube has a downstream end mounted in a fixed manner on a base (attachment ensuring tightness), said base having an outer diameter mounted in an inner diameter of a passage bushing, the inner diameter of the passage bushing being sufficiently great so that the upstream end of the tube is suitable to fit through the inner diameter of the passage bushing, the probe also comprising a measurement chamber having an end connected to the base.

Due to these features, it is possible to extract the tapping tube from the outside of the conduit without having to access inside said conduit, simply by removing the tapping tube and the base whereto it is attached outside the passage tube.

Preferentially, the end of the tapping tube is curved.

According to one embodiment, the base has a flared part which is inserted in a corresponding flared part of the passage bushing.

Advantageously, the flared part of the base is held firmly in place resting on the flared part of the passage bushing by means of a nut.

Preferentially, the measurement chamber has an end tapered with a nozzle, said nozzle being held firmly in place resting on the flared part of the base by means of the nut.

Due to these features, a simple and easy to disassemble assembly of the tapping tube is performed in the gas stream. In order to disassemble the tapping tube, it is simply necessary to unfasten the nut holding the nozzle of the measurement chamber in place on the flared part of the base, which releases said base and makes it possible to remove it via the inner diameter of the passage bushing.

In one preferential embodiment, the iso-kinetic probe according to the invention comprises, provided in the measurement chamber, static pressure, total pressure and temperature measurement means.

The total pressure measurement means is, for example, a Pitot tube.

The temperature measurement means consists, for example, of a thermocouple.

Determining the three parameters, total pressure, static pressure and temperature makes it possible to calculate the flow rate. The flow rate value obtained makes it possible to obtain the gas velocity for a given geometry in the measurement chamber. Determining the gas velocity in the measurement chamber makes it possible, by means of flow rate conservation equations, to calculate the upstream gas velocity, i.e. at the tapping tube orifice.

Advantageously, the iso-kinetic probe comprises several tapping tubes having curved ends of different diameters, said tapping tubes each being mounted on a base of a common outer diameter, said diameter being sufficiently great so that the curved end of the tube with the greatest diameter is suitable to fit through the inner diameter of the passage bushing.

In this way, it is possible to adjust the gas entry velocity in the tapping tube easily by changing the tube. This operation may be performed quickly because, as explained above, the tapping tube may be disassembled easily and quickly from the outside.

It is also possible to adjust the gas intake velocity at the tapping tube orifice by means of an intake pump connected to the measurement chamber. This pump makes it possible to accelerate the air velocity at the sampling tube inlet and therefore render said velocity equal to the velocity of the air in the conduit.

According to another embodiment, the iso-kinetic probe comprises a diaphragm making it possible to vary the passage cross-section at the inlet of the end of the air tapping tube. Due to the presence of this diaphragm, which may be actuated from the outside of the conduit, it is possible to vary the passage cross-section available to the gases and, as a result, the velocity of the gas at the tapping tube orifice continuously.

Other features and advantages of the present invention will emerge on reading the following description of an example of an embodiment given as an illustration with reference to the appended figures. In these figures.

Figure 1:
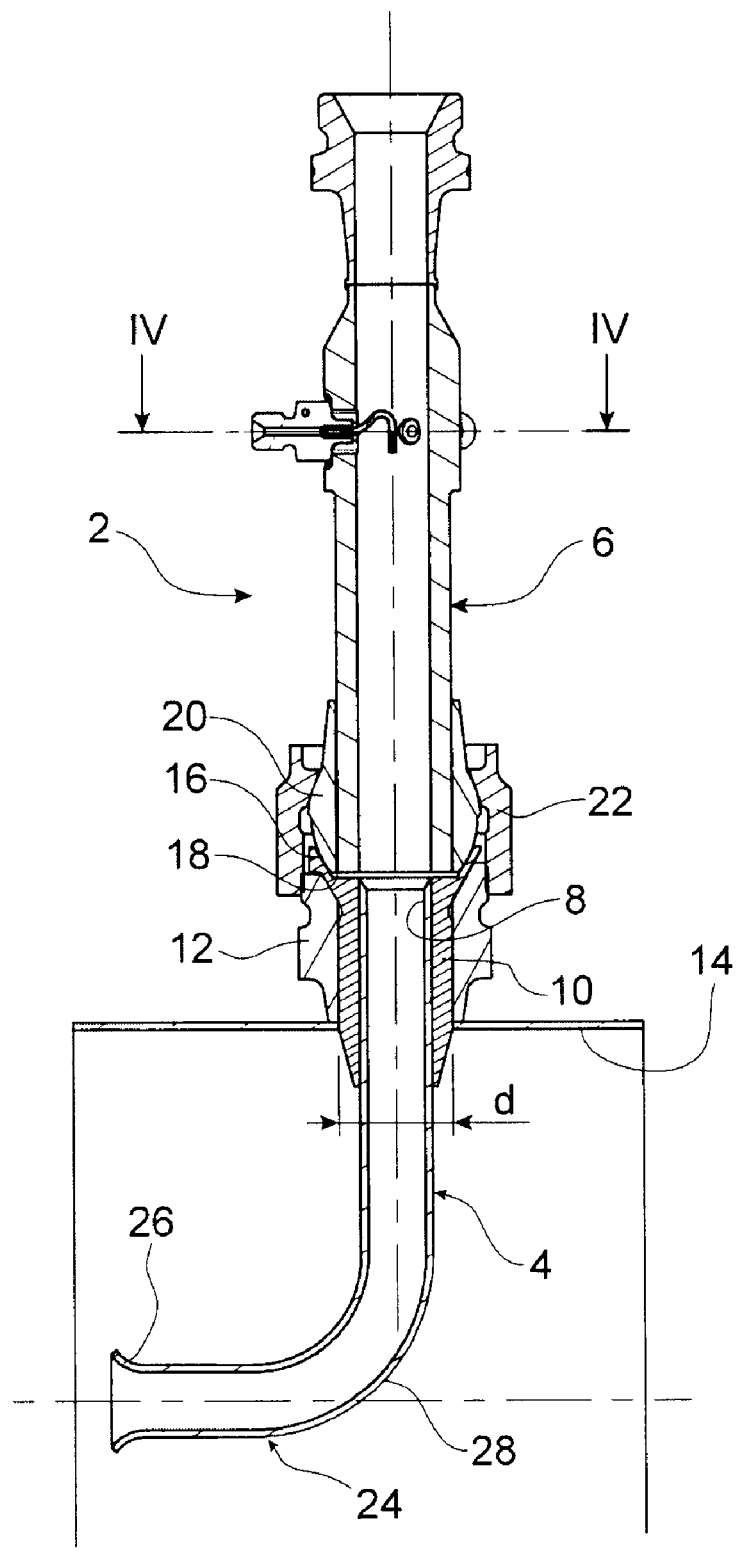
FIG. 1 is an overall sectional view or an iso-kinetic probe according to the present invention.

The iso-kinetic probe according to the invention, referred to using the general reference 2, consists of a tapping tube 4 and a measurement chamber 6. The tapping tube 4 comprises a downstream end 8 wherein the base 10 is attached. The base 10 is for example soldered or welded to the end 8 of the tapping tube. The base 10 has an outer diameter which is adjusted in the inner diameter of a passage bushing 12. The passage bushing 12 is in turn fixed, for example welded or soldered, outside a large-diameter conduit 14.

The base 10 comprises a flared end, conical in the embodiment represented 16. This conical part rests on a complementary conical part 18 of the passage bushing 12. The lower end of the measurement chamber comprises a nozzle 20 which rests against the inner part of the conical part 16. The nozzle 20 is in turn held in place tightened by a nut 22. In this way, the conical part 16 is held between the conical part 18 of the passage bushing 12 and the conical end of the nozzle 20.

Figure 2:
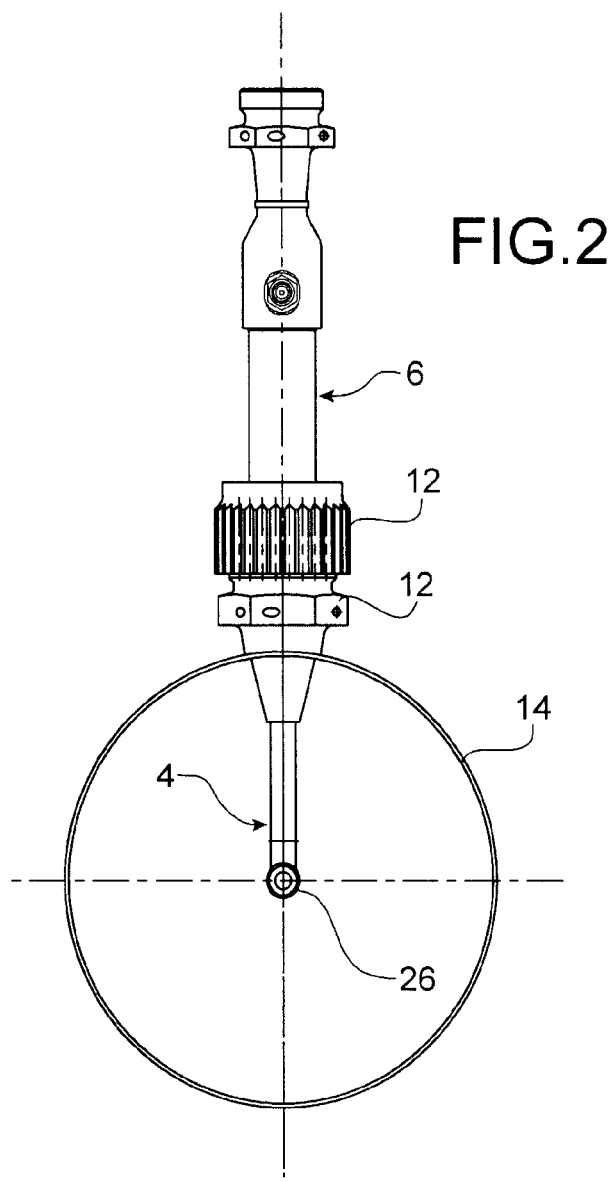
FIG. 2 is an external view of the iso-kinetic probe represented in FIG. 1.
Figure 3:
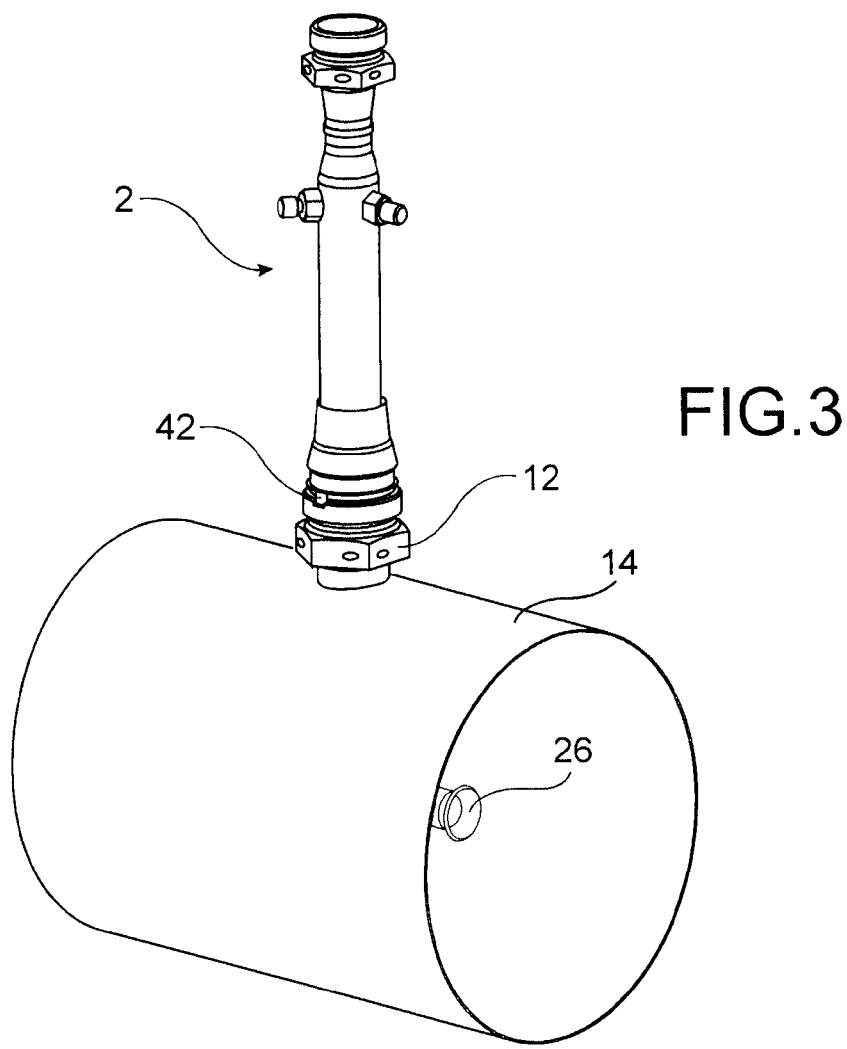
FIG. 3 is a perspective view of the iso-kinetic probe represented in FIGS. 1 and 2.
Figure 6:
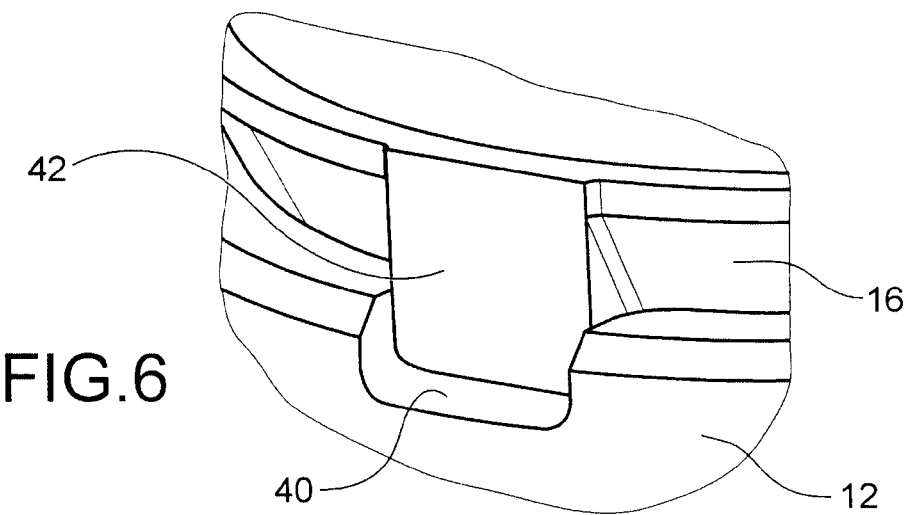
FIG. 6 is a detailed view of a polarisation and anti-rotation system.

The tapping tube 4 has an upstream end 24 comprising an orifice 26 and a curved part 28. As can be seen in FIGS. 2 and 3, the conduit 14 displays a circular cross-section and the orifice 26 is located at the centre of the circular cross-section of the conduit 14.

The tapping tube is extracted as follows. First of all, the nut 22 which comprises a threaded part engaged with the passage bushing 12 is unfastened and removed. Once the nut has been unfastened, the measurement chamber 6 is removed which releases the base 10. It is then possible to remove the entire tapping tube 4 by inserting it through the passage bushing 12. It is important to note that, to this end, the inner diameter d of the bore provided in the passage bushing is sufficiently great to enable the passage of the curved part 28 of the tube and the orifice 26 thereof, which has a flared shape.

The reassembly of the tube, or the assembly of a new tube, is performed in reverse. It is thus observed that it is possible to change the tapping tube 4 rapidly without having access to the inside of the conduit 14.

Figure 4:
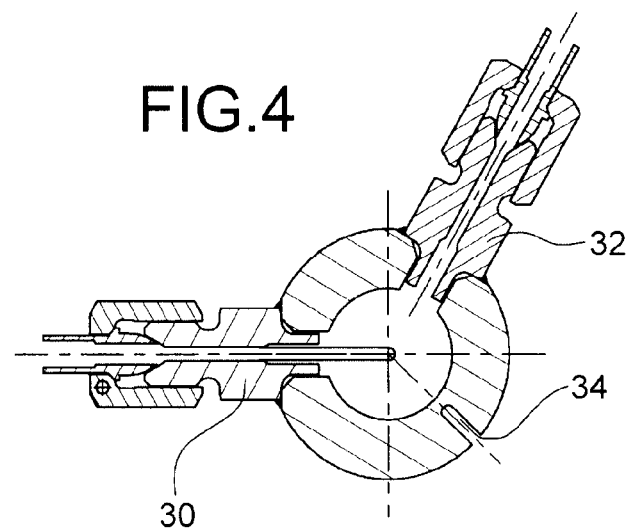
FIG. 4 is a sectional view along the plane IV-IV of FIG. 1.
Figure 5:
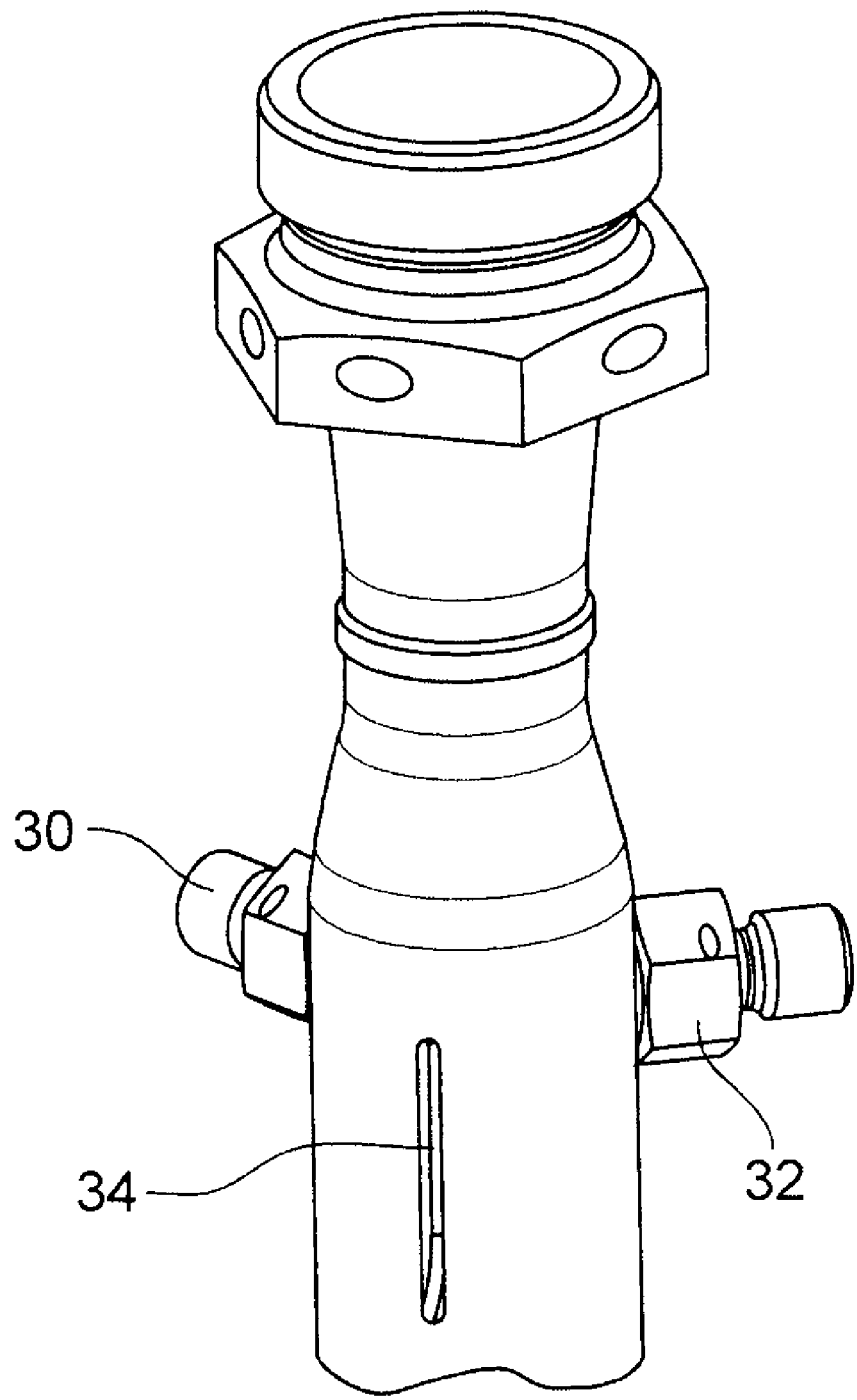
FIG. 5 is an outer perspective view of the upper end of the probe according to the invention.

FIG. 4 represents a sectional view along the plane IV-IV of FIG. 1, and FIG. 5, an external perspective view of measurement means. These measurement means comprise total pressure measurement means consisting of a Pitot tube 30, static pressure measurement means consisting by a static pressure sensor 32 and temperature measurement means.

Determining the total pressure, static pressure and temperature makes it possible to calculate the flow rate by means of Bernoulli equations. Determining the flow rate makes it possible to calculate the velocity for a given geometry. Determining the velocity of the fluid at the measurement chamber makes it possible, by means of flow rate conservation equation, to determine the upstream velocity, i.e. at the orifice 26 of the tapping tube 4.

In order to guarantee an angular orientation of the orifice 26 of the perfectly aligned hole with the longitudinal axis of the circular conduit 14, angular orientation means were provided. In the example of an embodiment represented, these means consist of a groove 40 formed from the passage bushing 12 and by a pin 42 formed in the conical part 16 of the base 10. When the pin 42 is inserted in the groove 40, it is ensured that the orifice 26 has the correct angular orientation with respect to the conduit 14. Moreover, the pin 42 prevents the tapping tube from rotating with respect to the passage bushing 12. Therefore, the pin 42 simultaneously provides an anti-rotation function.

Figure 9:
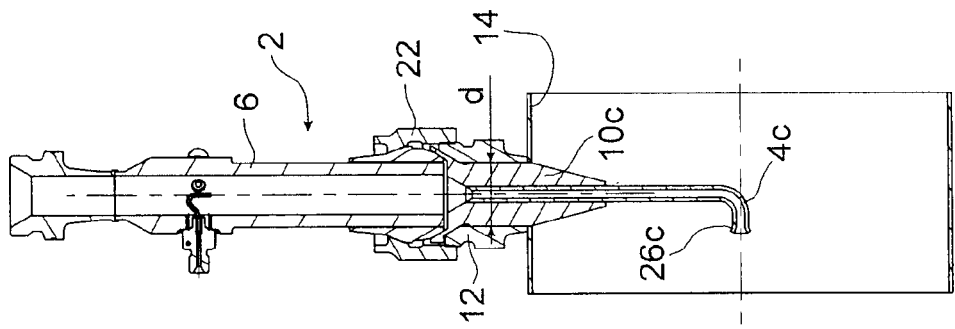
FIGS. 7 to 9 are three sectional views of an iso-kinetic probe according to the present invention with decreasing tapping tube diameters.
Figure 8:
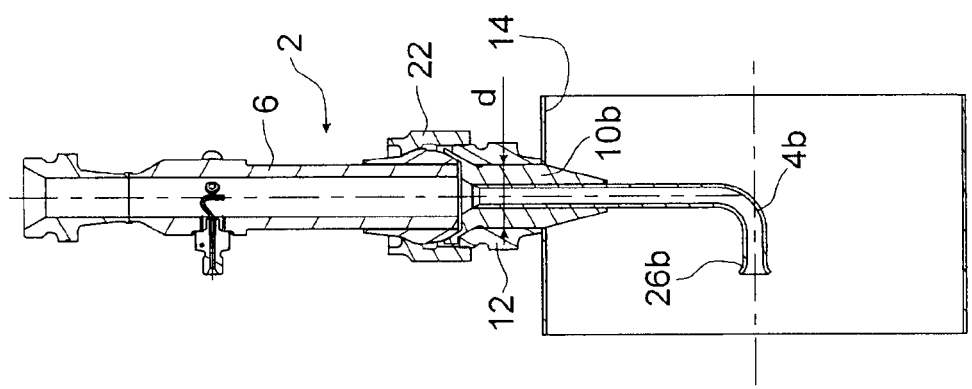
Figure 7:
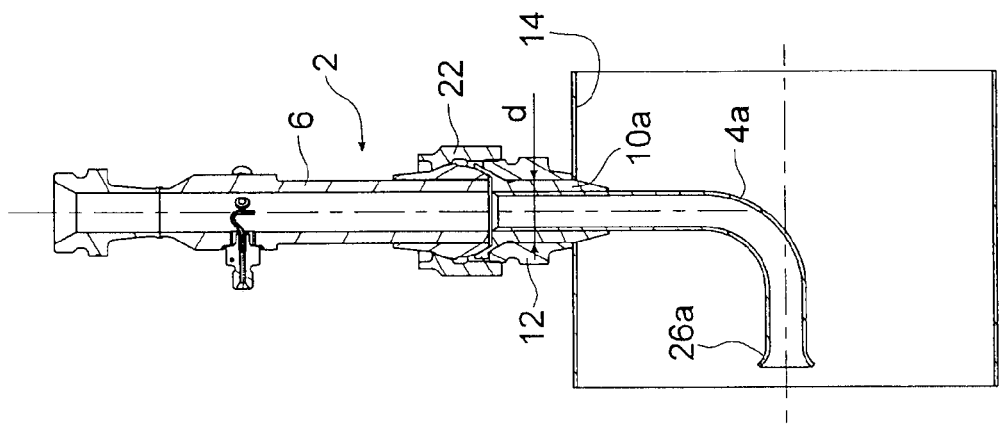

FIGS. 7, 8 and 9 represent three views of the same iso-kinetic probe according to the present invention equipped with tapping tubes 4a, 4b and 4c of different diameters. The tube with the greatest diameter is tube 4a. Its diameter is greater than that of tube 4b which in turn has a greater diameter than that of tube 4c. On the other hand, the outer diameter d of the various bases 10a, 10b and 10c is the same. In this way, it is possible to fit in the iso-kinetic probe 2 tubes of different diameters, which makes it possible to adjust the velocity in the orifice 26a, 26b or 26c. The velocity increases as the tube diameter decreases. Consequently, for a given pumping capacity, the probe with the greatest diameter will be selected for low air velocities in the tube (conversely, the smallest diameter will be selected for high air velocities in the tube). In order to replace one tube by another, the nut 22 is unfastened, the measurement chamber 6 is removed. The tapping tube 4a, 4b or 4c is then directly accessible. The outer diameter of the base 10a, 10b or 10c may slide freely in the inner diameter of the passage bushing 12. It is observed that the inner diameter d of the passage bushing 12 is provided to be sufficiently great so that the tube with the greatest diameter, in this case, the tube 4a, can fit in the bore provided in the passage bushing. The tapping tube to be replaced having been removed, another passage tube, for example the tube 4b or 4c is positioned and the measurement chamber 6 is put back in place and the nut 22 is refastened. The change is thus completed. It should be noted that this change is performed rapidly, ensuring the tightness of the assembly and without having access to the inside of the conduit 14.

The invention claimed is:

1. An iso-kinetic probe for the analysis of the pollution of gases generated by an aircraft engine, comprising:
   an air tapping tube having an upstream end and a downstream end;
   a base attached to the downstream end of the tube, said base including an outer diameter, an inner diameter, and a conical part with an inner face and an outer face;
   a passage bushing which is fixed on a conduit in which a gas stream flows, said passage bushing including an inner diameter d and a conical part;
   a measurement chamber with a nozzle provided on a lower end, the nozzle including a conical end; and
   a nut which holds the nozzle such that the nozzle rests on the conical part of the base, the nut including a threaded part which is engaged with the passage bushing,
   wherein the outer diameter of said base is mounted in the inner diameter of the passage bushing, the inner diameter of the passage bushing being sufficiently sized so that the upstream end of the tube is suitable to fit through the inner diameter of the passage bushing, and
   wherein an outer face of the conical end of the nozzle abuts the inner face of the conical part of the base and the conical part of the passage bushing abuts the outer face of the conical part of the base, such that the conical part of the base is sandwiched between the conical part of the passage bushing and the conical end of the nozzle.

2. The iso-kinetic probe according to claim 1, wherein the upstream end of the air tapping tube is curved.

3. The iso-kinetic probe according to claim 1, further comprising static pressure, total pressure and temperature measurement means provided in the measurement chamber.

4. Iso-kinetic probe according to claim 3, wherein the total pressure measurement means is a Pitot tube.

5. The iso-kinetic probe according to claim 3 or 4, wherein the temperature measurement means consists of a thermocouple.

6. The iso-kinetic probe according to any of claims 1 or 2, further comprising attaching one of several tapping tubes having upstream ends of different diameters, said tapping tubes each being mounted on the base, the diameter of the base being sufficiently sized so that a curved end of the tube with the greatest diameter is suitable to fit through the inner diameter of the passage bushing.

7. The iso-kinetic probe according to any of claims 1 or 2, further comprising at least one intake pump connected to the measurement chamber, said pump adjusts a gas intake velocity of an orifice of the air tapping tube.

8. The iso-kinetic probe according to any of claims 1 or 2, further comprising a diaphragm which varies a passage cross-section at an inlet of the upstream end of the air tapping tube.

9. The iso-kinetic probe according to claim 1, further comprising a groove provided in the passage bushing, and a pin provided in the conical part of the base, the pin cooperating with the groove.

* * * * *